United States Patent [19]

Martin et al.

[11] 4,319,022

[45] Mar. 9, 1982

[54] 2-O-SUBSTITUTED SULFONYL DERIVATIVES OF FORTIMICIN B

[75] Inventors: Jerry R. Martin; John S. Tadanier, both of Waukegan; Paulette Collum, Zion, all of Ill.

[73] Assignee: Abbott Laboratories, North Chicago, Ill.

[21] Appl. No.: 131,468

[22] Filed: Apr. 27, 1980

Related U.S. Application Data

[62] Division of Ser. No. 863,009, Dec. 21, 1979, Pat. No. 4,169,198.

[51] Int. Cl.³ .................. A61K 31/71; C07H 15/22

[52] U.S. Cl. .................. 536/17 R; 424/180; 424/181

[58] Field of Search .................. 536/17 R, 17 B

[56] References Cited

U.S. PATENT DOCUMENTS 4,176,178 11/1978 Martin et al. .................. 536/17 B Primary Examiner—Johnnie R. Brown
Attorney, Agent, or Firm—Robert L. Niblack; Gildo E. Fato; Joyce R. Niblack

[57] ABSTRACT

A new fortimicin antibiotic, 2-deoxyfortimicin B, intermediates useful in the preparation of the compound, methods of making and using the compound and compositions containing 2-deoxyfortimicin B.

7 Claims, No Drawings

2-O-SUBSTITUTED SULFONYL DERIVATIVES OF FORTIMICIN B

This is a division of application Ser. No. 863,009, filed Dec. 21, 1979, now U.S. Pat. No. 4,169,198.

BACKGROUND OF THE INVENTION

Despite the availability of a variety of highly effective antibiotics, the search for new antibiotics is a continuing one. The primary reason for the continuing search is the reoccurring development of microorganisms which are resistant to existing antibiotic therapy. Thus, there is a continuing need for new antibiotics which are either intrinsically more active than existing drug entities and thus can be administered in lower dosages to minimize the side effects of these powerful drugs, or are effective against resistant strains.

A number of aminoglycoside antibiotics are known, such as the gentamicin and kanamycin family of antibiotics. More recently, a new family of aminoglycosides, the fortimicins have been identified. See, for example, U.S. Pat. Nos. 3,976,768 and 3,931,400.

Although the fortimicin family is a relatively new group of antibiotics, clinical experience has shown that aminoglycoside antibiotics are susceptible to resistant strain development. In many cases, the resistance is R-factor mediated and is attributed to the ability of the bacteria to enzymatically modify the amino or hydroxy groups of the aminoglycoside antiobiotics.

Thus, there is a continuing need for new antibiotic entities in this valuable antibiotic family. The present invention provides one such entity.

SUMMARY OF THE INVENTION

This invention relates to a new, synthetic fortimicin derivative, 2-deoxyfortimicin B. In addition to its antibiotic properties, the compound of this invention is useful as an intermediate in the synthesis of 2-deoxyfortimicin A. Intermediates are also provided as well as pharmaceutical compositions and methods.

DETAILED DESCRIPTION OF PREFERRED EMBODIMENTS

The compound of this invention, 2-deoxyfortimicin B, is represented by Formula I:

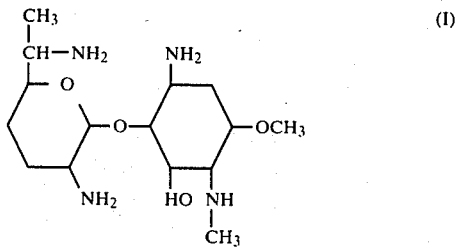

2-Deoxyfortimicin B exhibits anti-bacterial activity against various Gram-positive and Gram-negative bacteria. The antibiotic can be employed in daily dosages of from 10 to 200 mg/kg, by parenteral routes of administration, i.e., by intramuscular, intravenous, subcutaneous and intraperitonal routes, for a period of time sufficient to provide an antibiotic effect, generally, for a period of time following the disappearance of infection symptoms. Additionally, the anti-bacterial agent of this invention can be incorporated into anti-bacterial or disinfecting solutions which are used as a surface disinfectant for controlling the population of various bacteria.

2-Deoxyfortimicin B is also useful as an intermediate for 2-deoxyfortimicin A which is a new antibiotic disclosed in our copending U.S. patent application concurrently filed and co-assigned.

The pharmaceutically acceptable salts of 2-deoxyfortimicin B are also included within the scope of this invention. The term "pharmaceutically acceptable salts" refers to non-toxic acid addition salts which are prepared by reacting the base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like salts.

The present invention further provides new derivatives of fortimicin B useful as intermediates in preparing 2-deoxyfortimicin B and represented by Formulae II, III and IV.

Compounds of formula II are 2-O-hydrocarbonsulfonyl derivatives represented as follows:

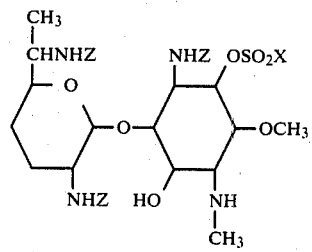

wherein X is a straight, branched or cyclic saturated or unsaturated hydrocarbon moiety having from 1 to 8 carbon atoms and Z is benzyloxycarbonyl;

Compounds of Formula III are the cyclic 4,5-oxazolidine derivatives of the compounds of formula II:

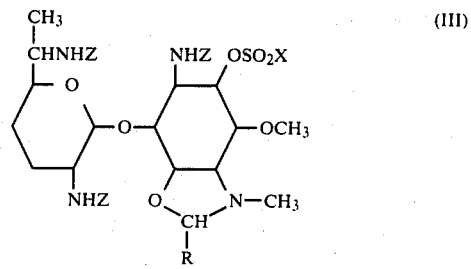

wherein X is as defined above, Z is benzyloxycarbonyl and R is hydrogen, loweralkyl, aryl or substituted aryl.

The 2-O-hydrocarbon sulfonyl derivatives are those derived from hydrocarbon sulfonic acid having up to 8 carbon atoms, such as methanesulfonic acid, ethanesulfonic acid, benzenesulfonic acid, toluenesulfonic acid, i.e., compounds of Formulae II and III wherein X is lower alkyl, loweralkenyl, lower alkynyl, aryl, aralkyl and the like.

The term "lower alkyl" refers to straight or branched chain alkyl radicals having from 1 to 6 carbon atoms, i.e., methyl, ethyl, n-propyl, iso-propyl, n-butyl, sec-butyl, tert-butyl, n-pentyl, 2-methylbutyl, n-hexyl, 2-methylpentyl, 3-methylpentyl, 2,2-dimethylbutyl and the like.

The term "loweralkenyl" refers to $C_2$ to $C_6$ alkenyl moieties, i.e., ethenyl, propenyl, n-butenyl, n-pentenyl, n-hexenyl and the like.

The term "loweralkynyl" refers to $C_2$ to $C_6$ alkynyl groups, i.e., ethynyl, propynyl, 2-butynyl, 2-pentynyl, etc.

"Aryl" as used herein, refers to aromatic hydrocarbons such as benzyl, phenyl, tosyl, toluyl and the like.

Aralkyl includes, but is not limited to aromatic hydrocarbons having lower alkyl sidechains, i.e., 1-methylphenyl, 2-butylphenyl, and the like.

1,2-epiminofortimicin B is also provided by the present invention. The compound is represented by Formula IV:

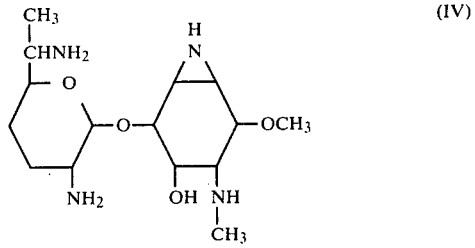

2-deoxyfortimicin B can be prepared as follows. In one process, fortimicin B, having all primary amino groups protected by benzyloxycarbonyl groups and the $C_5$ hydroxyl and $C_4$ secondary amino group blocked by a suitable aldehyde to form an oxazolidine ring, upon treatment with a hydrocarbonsulfonyl halide or anhydride, is converted to a 2-O-methanesulfonyl ester (e.g., to a 2-O-methanesulfonyl ester) which in turn is converted to a 1, 2', 6'-tri-N-benzyloxycarbonyl-2-O-hydrocarbonsulfonyl ester derivative following acid hydrolysis of the oxazolidine ring, which is N-deblocked by catalytic hydrogenolysis in the presence of an acid. When the resulting 2-O-hydrocarbonsulfonylfortimicin B salt is converted to the free base, the intermediate 1,2-epiminofortimicin B is obtained. Continuing the process, catalytic hydrogenolysis of 1,2-epiminofortimicin B gives 2-deoxyfortimicin B which in turn is converted is 2-deoxyfortimicin A.

In an alternate procedure the key intermediate 1,2-epiminofortimicin B is conveniently prepared as follows. Fortimicin B, having all primary amino groups protected by Schiff base formation from a suitable aldehyde (e.g., benzaldehyde) and the $C_5$ hydroxyl and $C_4$ secondary amino group protected by the same aldehyde to form an oxazolidine ring, upon treatment with a hydrocarbonsulfonyl halide or anhydride, is converted to a 2-O-hydrocarbonsulfonyl ester which in turn is converted, on acid hydrolysis of the Schiff base and oxazolidene to a 2-O-hydrocarbonsulfonylfortimicin B salt. The salt upon conversion to the free base rearranges to 1,2-epiminofortimicin B.

The following Examples further illustrate the present invention.

EXAMPLE 1

1,2', 6'-Tri-N-benzyloxycarbonylfortimicin B

To a stirred solution of 2.0 g of fortimicin B 30 ml of water and 60 ml of methanol, cooled in an ice bath, is added 4.44 g of N-(benzyloxycarbonyloxy)succinimide. Stirring is continued at 0° for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromatographed on silica gel. Elution with a solvent system composed of chloroform-methanol-ammonium hydroxide (234:1.4:0.1 v/v/v) gives 1.05 g of 1, 2', 6'-tri-N-benzyloxycarbonylfortimicin B: $[\alpha]_D^{25} - 16.5°$ (c 1.0, $CH_3OH$); $IR(CDCl_3)$ 1712 and 1507 $cm^{-1}$; NMR $(CDCl_3)$ 1.03 ($C_{6'}$—$CH_3$, $J_{6',7'} = 6.0$ Hz), 2.32 ($C_4$—$NCH_3$), 3.41 ($OCH_3$).

Anal. Calcd. for $C_{39}H_{50}N_4O_{11}$:C,62.39; H, 6.71; N,7.46. Found: C,62.16; M,6.76; N,7.43.

EXAMPLE 2

1,2',6'-Tri-N-benzyloxycarbonyl-4,5-salicylaldehyde oxazolidine fortimicin B

A solution of 22 g of 1,2',6'-tri-N-benzyloxycarbonyl-fortimicin B in 396 ml of methanol is treated with 3.96 ml of salicylaldehyde and refluxed for 1 hour. Evaporation of the reaction mixture under reduced pressure gives 26 g of 1,2',6'-tri-N-benzyloxycarbonyl-4,5-salicylaldehyde oxazolidine fortimicin B as a brownish yellow solid: $NMR(CDCl_3)$ $\delta 0.94$ ($C_{6'}$—$CH_3$, $J_{6',7'} = 7.0$ Hz), 2.34 ($C_4$—$NCH_3$), 3.49 ($C_3$—$OCH_3$), 7.31 (Cbz)

EXAMPLE 3

1,2',6'-Tri-N-benzyloxycarbonyl-4,5-(2-O-methanesulfonylsalicylaldehyde)-oxazolidine-2-O-methanesulfonylfortimicin B A stirring solution of 26 g of 1,2',6'-tri-N-benzyloxycarbonyl-4,5-salicylaldehyde oxazolidine fortimicin B in 154 ml of dry pyridine is treated with 12.26 ml of freshly distilled methanesulfonylchloride. After stirring for 20 hours the reaction mixture is poured into 2000 ml of 5% sodium hydrogen carbonate solution and extracted 2 times with 1000 ml portions of chloroform. The combined chloroform extract is washed with 1000 ml of 5% sodium hydrogen carbonate and then twice with 1000 ml portions of water. The chloroform is evaporated under reduced pressure and the pyridine is removed by repeated codistillation with benzene to give 31.2 g of 1,2',6'-tri-N-benzyloxycarbonyl)-4,5-(2-O-methanesulfonylsalicylaldehyde)oxazolidine-2-O-methanesulfonylfortimicin B:NMR $(CDCl_3)$ $\delta 1.0$ ($C_{6'}$—$CH_3$, $J_{6'7'} = 7.0$ Hz), 2.19 ($C_4$—$NCH_3$), 2.94 ($C_2$—$OSO_2CH_3$), 3.15 (Ar—$OSO_2CH_3$), 3.60 ($C_3$—$OCH_3$), 7.33 (Cbz).

EXAMPLE 4

1,2',6'-Tri-N-benzyloxycarbonyl-2-O-methanesulfonylfortimicin B

A stirring solution of 31.2 g of 1,2'6'-tri-N-benzyloxycarbonyl-4,5-(2-O-methanesulfonylsalicylaldehyde) oxazolidine-2-O-methanesulfonylfortimicin B in 1000 ml of tetrahydrofuran is treated with 262 ml of 0.4 N hydrochloric acid. After stirring for 4 hours, the reaction mixture is poured into 5700 ml of 6 N ammonium hydroxide solution and extracted 2 times with 1400 ml portions of chloroform. The combined chloroform extract is washed with 5700 ml of 7% sodium hydrogen sulfite solution and then 2 times with 1180 ml portions of water. Removal of the chloroform under reduced pressure gives 27.35 g. of crude 1,2',6'-tri-N-benzyloxycarbonyl-2-O-methanesulfonylfortimicin B. The crude material is chromatographed on a column (6.0×80 cm)

of Sephadex LH-20 gel prepared and eluted with 95% ethanol. Fractions containing the desired material are combined and concentrated to dryness under reduced pressure to give pure 1,2',6'-tri-N-benzyloxycarbonyl-2-O-methanesulfonylfortimicin B as a glass: $[\alpha]_D^{23}+18.5°$ (c 1.0, $CH_3OH$); IR ($CDCl_3$) 3436, 3350, 1703, 1502, 1354 and 1173 $cm^{-1}$; NMR($CDCl_3$) δ1.07 ($C_6$—$CH_3$, $J_{6',7'}=7.0$ Hz) 2.34 ($C_4$—$NCH_3$), 2.87 ($OSO_2CH_3$), 3.48 ($OCH_3$).

Anal Calcd. for $C_{40}H_{52}N_4O_{13}S$: C, 57.96; H, 6.32; N, 6.76. Found: C, 57.65; H, 6.52; N, 6.62.

EXAMPLE 5

2-O-Methanesulfonylfortimicin B Tetrahydrochloride

A solution of 4.42 g of 1,2',6'-tri-N-benzyloxycarbonyl-2-O-methanesulfonylfortimicin B in 310 ml of 0.2 N hydrochloric acid in methanol is treated for 4 hours with 4.5 g of 5% palladium on carbon under hydrogen and 3 atmospheres of pressure. The catalyst is filtered off and washed with ethanol. The filtrate is concentrated to dryness under reduced pressure and the excess hydrochloric acid is removed by repeated co-distillation with methanol to leave 2.79 g of 2-O-methanesulfonylfortimicin B tetrahydrochloride as a white glass: $[\alpha]_D^{25}+91.7°$ (c 1.01, $CH_3OH$); IR (KBr) 3400, 2920, 1590, 1330 and 1165 $cm^{-1}$; NMR($D_2O$) δ1.82 ($C_{6'}$—$CH_3$, $J_{6'7,}=7.0$ Hz), 3.31 ($C_4$—$NCH_3$), 3.88 ($C_2$—$OS_2CH_3$), 4.07 ($C_3$—$OCH_3$), 5.88 ($C_1H$, $J=4.0$ Hz)

EXAMPLE 6

1,2-Epiminofortimicin B

A solution prepared from 2.8 g of 2-O-methanesulfonylfortimicin B tetrahydrochloride in 20 ml of water is passed through a column (2.2×20 cm) of an anion exchange resin quarternary ammonium sytrene type, e.g., AG ®2-X8, 50-100 mesh resin, (OH form) sold by Bio-Rad laboratories, sufficient to remove the chloride ion. Basic elutes are combined and allowed to stand at room temperature for 72 hours. Evaporation of the water under reduced pressure leaves 3.0 g of 1,2-epiminofortimicin B: NMR($D_2O$) δ1.55 ($C_{6'}$—$CH_3$, $J_{6',7'}=7.0$ Hz), 2.83 ($C_4$—$NCH_3$), 4.02 ($C_3$—$OCH_3$), 5.42 ($C_1H$, $J=3.0$ Hz).

EXAMPLE 7

2-Deoxyfortimicin B and 1-Deamino-2-deoxy-2-epi-aminofortimicin B

A solution prepared from 3.22 g of 1,2;-epiminofortimicin B in 250 ml of wet ethanol is treated for 24 hours with 12 g of Raney nickel under 3 atmospheres of hydrogen. The catalyst is collected on a filter and washed with ethanol. The filtrate is concentrated to dryness under reduced pressure to give 2.90 g of a mixture of 2-deoxyfortimicin B and 1-deamino-2-deoxy-2-epi-aminofortimicin B as a white froth. The mixture is chromatographed on a column (2.9×50 cm) of a cation exchange resin, ($NH_4^+$ form) (e.g., BioRad 70 100-200 mesh, carboxylic styrene type resin sold by Bio-Rad Laboratories, and eluted with a gradient of water to 1 N ammonium hydroxide. The first elutes are taken to dryness under reduced pressure to yield 1.347 g of pure 2-deoxyfortimicin B: NMR ($D_2O$) δ1.5 ($C_{6'}$—$CH_3$, $J_{6',7'}=7.0$ Hz), 2.82 ($C_4$—$NCH_3$), 3.86 ($C_3$—$OCH_3$), 5.48 ($C_1$, H, $J=3.5$ Hz).

Later elutes are collected and taken to dryness under reduced pressure to yield 1.172 g of 1-deamino-2-deoxy-2-epi-aminofortimicin B: NMR ($D_2O$) δ1.51 ($C_6,CH_3,J_{6',7'}=7.0$ Hz), 2.83 ($C_4$—$NCH_3$), 4.02 ($C_3$—$OCH_3$), 5.31 ($C_1,H$, $J=4.0$ Hz).

The in vitro antibiotic activity of 2-deoxyfortimicin B is determined by a two-fold dilution test using Mueller-Hinton agar, 10 ml per Petri plate. The inoculum of approximately $1\times10^5$ of the indicated test organism is delivered by the Steer's replicator. The test is incubated at 37° C. for 24 hours.

The compounds of this invention are active as systemic antibiotics when injected by parenteral routes of administration, i.e., by the intramuscular, intravenous, intraparitoneal or subcutaneous routes of administration. The compounds can also be administered orally in those instances where it is desirable to sterilize the intestinal tract and can additionally be applied topically or rectally.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized, by for example, filtration through a bacteria-retaining filter, by incorporating sterilizing agents into the compositions. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 10 to 200 mg/kg of body weight daily are administered to a mammalian patient suffering from an infection caused by susceptible organism.

We claim:

1. A compound of the formula:

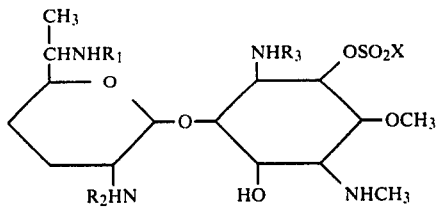

wherein each $R_1$, $R_2$ or $R_3$ are the same or different members of the group consisting of hydrogen or benzyloxycarbonyl and X is a hydrocarbon having from 1 to 8 carbon atoms, inclusive; or a pharmaceutically acceptable salt thereof when any of $R_1$, $R_2$ or $R_3$ are hydrogen.

2. A compound of claim 1 wherein $R_1$, $R_2$ and $R_3$ each are benzyloxycarbonyl.

3. A compound of claim 1 wherein X is loweralkyl, monocyclic aryl or monocyclic aralkyl.

4. A compound of claim 3: 1, 2′, 6′-tri-N-benzyloxycarbonyl-2-O-methanesulfonylfortimicin B.

5. A compound of claim 1 wherein $R_1$, $R_2$ and $R_3$ each are hydrogen.

6. A compound of claim 5 wherein X is loweralkyl, monocyclic aryl or monocyclic aralkyl.

7. A compound of claim 5: 2-O-methanesulfonylfortimicin B.

* * * * *